United States Patent [19]

Abbas et al.

[11] Patent Number: 5,223,402

[45] Date of Patent: Jun. 29, 1993

[54] METHOD OF DETECTING MICROBES UTILIZING CHEMILUMINESCENT COMPOUND

[75] Inventors: Charles A. Abbas; Ruth F. Eden, both of Ann Arbor, Mich.

[73] Assignee: Difco Laboratories, Ann Arbor, Mich.

[21] Appl. No.: 768,357

[22] Filed: Sep. 30, 1991

Related U.S. Application Data

[63] Continuation of Ser. No. 575,212, Aug. 30, 1990, abandoned.

[51] Int. Cl.$^5$ .................... C07C 13/68; C09K 3/00; C07D 305/04; C12Q 1/10
[52] U.S. Cl. .................................. 435/18; 435/19; 435/21; 536/18.1
[58] Field of Search ................ 435/21, 18, 19, 21; 536/18.1

[56] References Cited

U.S. PATENT DOCUMENTS

| | | | |
|---|---|---|---|
| 3,564,588 | 2/1971 | Soli | 435/34 |
| 3,959,081 | 5/1976 | Witz et al. | 435/34 |
| 4,925,789 | 5/1990 | Edberg | 435/38 |
| 4,931,223 | 6/1990 | Bronstein | 435/4 |
| 4,952,707 | 8/1990 | Edwards et al. | 435/4 |
| 4,959,182 | 9/1990 | Schaap | 435/21 |
| 4,962,192 | 10/1990 | Schaap | 536/4.1 |
| 4,978,614 | 12/1990 | Bronstein | 435/21 |

OTHER PUBLICATIONS

Rawn, 1983, Biochemistry p. 287, Harper & Row, New York.
Trepeta et al. (Feb. 1984) Methylumbelliferyl-β-D-Glucuronide-Based Medium for Rapid Isolation and Identification of *E. coli* J. Clin Microbiol 19:172-4.
Edberg et al. (Sep. 1986) Comparison of β--Glucuronidase-Based Substrate Systems for Identification of *E. coli* J. Clin Chem 24:368-371.
Edberg et al. (Jun. 1988) National Field Evaluation of Defined Substrate Method for the Simultaneous Enumeration of Total Coliforms and *E. coli* From Drinking Water: Comparison with the Standard Multiple Tube Fermentation Method. Appl. Environ. Microbiol 54:1595-1601.
Berg et al (Aug. 1988) Rapid Detection of Total and Fecal Coliforms in Water by Enzymatic Hydrolysis ... Appl Env Micro 54:2118-2122.
Schaap et al. (Sep. 1989) Chemiluminescent Substrates for Alkaline Phosphatase: Application to Ultrasensitive Enzyme-Linked) Immunoassays and DNA Probes Clin. Chem 35:1863-4.
Schaap et al. (1987) Chem. and Enzymatic triggering of 1,2-dioxetanes 3: Alkaline phosphatase catalyzed chemiluminescence from aryl phosphate-substituted dioxetane. Tetrahedron Lett 28:1159-62.

*Primary Examiner*—Michael G. Wityshyn
*Assistant Examiner*—Louise N. Leary
*Attorney, Agent, or Firm*—Reising, Ethington, Barnard, Perry & Milton

[57] ABSTRACT

A method of detecting, identifying, and enumerating microbes in biological and non-biological samples includes the steps of combining the sample with a triggerable chemiluminescent compound specifically susceptible to the initiation of chemiluminescent decomposition by at least one microbial enzyme in the sample and detecting and integrating light emission over an extended period of time as an indication of the presence, identification, or enumeration of the microbes in the sample.

16 Claims, No Drawings

METHOD OF DETECTING MICROBES UTILIZING CHEMILUMINESCENT COMPOUND

This application is a continuation of Ser. No. 575,212, filed Aug. 30, 1990, now abandoned.

TECHNICAL FIELD

The present invention relates to the detection and identification of microbes in biological and nonbiological samples. More specifically, the present invention provides a method particularly well suited for detecting the presence of microbial contamination in food stuffs, clinical samples and the like.

BACKGROUND ART

It is desirable to provide rapid detection, identification, and/or enumeration of microorganisms in biological and nonbiological samples. While a number of tests have been developed for a variety of markets using a number of widely varying methodologies, there continues to be a need for simple, rapid, inexpensive, sensitive, and specific detection tests. Examples of presently used tests are DNA probes, immunoassays, electrical measurements, ATP measurements, and enzymatic substrate tests. Currently, the most sensitive tests do not readily detect less than $10^5$ cfu/ml. Since bacteria are not readily found in those concentrations in food, clinical, environmental, etc. samples, most tests require an overnight pre-enrichment step using conventional culture media to allow the sufficient growth and division of these microorganisms. In other words, a sample is taken and must be cultured in order to allow growth and multiplication of the microorganisms in the sample to a quantity detectable by present day technology.

New emerging detection methods for bacteria have greater predicted sensitivity than those presently on the market. These technologies are predicting sensitivities of $10^1 - 10^3$ cfu/ml. As a result, these technologies can considerably shorten but not totally eliminate the pre-enrichment step. Since none of these methods can address the diverse market needs, and as of yet have not been proven in the marketplace, new additions to these methods and further improvements of the existing methods are still in need.

An example of an enzymatic substrate test is the "MUG Test" that was first proposed in 1982 by Feng et al, "Fluorogenic assays for immediate confirmation of *Escherichia coli*", *Applied and Environmental Microbiology*, Vol. 43, 1982, pp. 1320-1329. The MUG test facilitated the detection of *E. coli*, although it improved total coliform detection very little.

Edberg and collaborators modified the "MUG Test" by devising a minimal culture medium, similar to those used for many years by bacterial geneticists. Edberg, S. C. et al, "National Field Evaluation of a Defined Substrate Method for the Simultaneous Enumeration of Total Coliforms and *Escherichia coli* from Drinking Water," *Applied and Environmental Microbiology*, Vol. 54, 1988, pp. 1595-1601, correction p. 3197. In this technology, the culture medium contains little in the way of organic nutrients except for 4-methylumbelliferyl-b-D-glucuronide (MUG) and a second substrate, o-nitrophenyl-b-D-galactoside (ONPG).

The problem with *E. coli* detection based on MUG hydrolysis is that the glucuronidase gene (uid A) seems to be present in the *E. coli*, but is not expressed in many of the strains, including some of the pathogenic strains. Feng, et al, "Presence of b-D-Glucuronidase Gene Sequences in MUG Assay $(-)$ *Escherichia coli*", *Abstracts of the 90th Annual Meeting of the American Society for Microbiology*, 1990, Abstract Q-7, p. 289; Hartman, P. A., "The MUG (Glucuronidase) Test for *Escherichia coli* in Food and Water," in A. Balows, R. C. Tilton, and A. Turano, Ed., *Rapid Methods and Automation in Microbiology and Immunology*, Brixia Academic Press, Brescia, Italy, 1989, pp. 290-308. In some media, inhibition of glucuronidase synthesis by lactose may occur, but other factors which are currently not totally understood may also be involved.

Others have reported various other methods of detecting and identifying *E. coli* from bacterial colonies. Edberg et al in "Comparison of—glucuronidase-based substrate systems for identification of *Escherichia coli*, *J. Clin. Microbiology*, Sept. 1986, pp. 368-371, discloses a method based on the measurement of beta glucuronidase which is claimed to be specific and inexpensive for the identification of *E. coli*. Restaino et al in "Use of Chromogenic Substrate 5-bromo-4-chloro-3-indolyl-B-D-glucuronide (X-GLUC) for enumerating *Escherichia coli* in 24 H from ground beef, *J. Food Protection*, Vol., 53, June 1990, pp. 508-510 discloses a 24 hour direct plating method for *E. coli* using the X-GLUC incorporated into a peptone-tergitolagar base.

These present methodologies for coliform and *E. coli* detection are marginal in performance.

The present invention recognizes that growing bacterial cells make use of approximately 1000 to 5000 enzymatically catalyzed reactions. Hydrolases constitute one of the largest groups of enzymes present in microorganisms. A strong correlation exists between the growth of bacteria and the detection of hydrolytic enzyme activity. As a result of this correlation, these enzymes have been extensively utilized to determine the presence and/or to identify microorganisms in biological and nonbiological samples. This approach to the detection of microorganisms is limited by the number of cells and their physiological state, sensitivity of the assay methods, types of substrates, and the enzymes being measured. Assay methods used are, for example, colorimetric, turbidometric, radiometric, fluorometric, and photometric.

Estimates of the cellular content of several proteins indicate that on the average $10^{-20}$ to $10^{-19}$ mole of any specific protein or enzyme is present per actively growing bacterial cell. Photometric measurements obtained with 1, 2-dioxetane chemiluminescent substrates of the enzymes alkaline phosphatase and beta-D-galactosidase detect $10^{-21}$ and $10^{-19}$ mole of these enzymes, respectively. Thus, it is theoretically possible to detect 1-100 cfu/ml of a sample with chemiluminescent 1,2-dioxetane enzyme substrates.

The U.S. Pat. No. 4,857,652 to Schaap, issued Aug. 15, 1989, discloses novel light producing 1,2-dioxetanes. These chemiluminescent compounds can be triggered by an activating agent to generate light. This mechanism for light production involves two steps. Step one involves the thermal or the enzyme catalyzed decomposition of a high energy material (generally a peroxide) yielding one of the reaction products in a triplet or singlet electronic excited state. The second step is the emission of a photon (fluorescence or phosphorescence) from this excited species producing the light observed from the reaction. As set forth by Schaap et al in Clinical Chemistry, Vol. 35, No. 9, 1989 (1863-1864), more than 350 papers have described investigations of these high energy peroxides which undergo spontaneous decomposition to generate chemiluminescence. Schaap et al developed new dioxetanes that are thermally very stable but can be chemically and enzymatically triggered to produce chemiluminescence on demand. Chemical or enzymatic removal of the protecting group from the stable dioxetane produces an unstable aryloxide dioxetane which decomposes to provide the observed chemiluminescence. This can be made pH dependent such that an enzyme can cause the stable form to become unstable in a neutral pH but light emission through energy transfer is only completed through changing the pH to an alkaline state. This change in pH is referred to as an enhancer system which provides a 400 fold increase in the chemiluminescence efficiency of the reaction in the presence of the enzyme alkaline phosphatase. Schaap et al recognized that the luminescent reaction can be used for ultrasensitive detection of phosphatase-linked antibodies and DNA probes. For example, the Photo Gene TM system manufactured by Life Technologies, Inc. of Gaithersburg, Md., utilizes such a chemiluminescent reaction for the detection of nucleic acids. Up until this time, these uses of the chemiluminescent dioxetanes have been limited to the detection of DNA probes and alkaline phosphatase-linked antibodies.

The present invention utilizes chemiluminescent compounds, such as 1,2-dioxetane derivatives, for the detection and identification of microorganisms in biological and nonbiological samples.

SUMMARY OF THE INVENTION

In accordance with the present invention, there is provided a method of detecting, identifying and enumerating microbes in biological and nonbiological samples, the method including the steps of combining the sample with a triggerable chemiluminescent compound specifically susceptible to the initiation of chemiluminescent decomposition by at least one microbial enzyme that is present in the sample and detecting and integrating light emission over an extended period of time as an indication of the presence of microbes in the sample.

DETAILED DESCRIPTION OF THE INVENTION

In accordance with the present invention, there is provided a method of detecting microbes in biological and nonbiological samples. In particular, such samples could be microbiological, industrial, clinical, environmental, or biotechnical. More specifically, the present invention is very well suited for rapid detection of microbes in food stuffs, such as in restaurants or homes. With regard to food stuffs, prior art methods required almost 24 hours for an analysis to be conducted because of the necessary enrichment periods needed to grow enough bacteria to reach the sensitivity level of those systems. The present invention provides increased sensitivity thereby necessitating much shorter incubation periods as discussed below. Accordingly, the present invention provides a significant advance in the detection of microbes in food stuff by being able to provide the necessary information regarding contamination during a period of time which could be used by a restaurant to remove food from availability prior to distribution to the public.

Generally, the subject method includes the steps of combining the sample with a triggerable chemiluminescent compound (CLC) specifically susceptible to the initiation of chemiluminescent decomposition by at least one microbial enzyme in the sample and then detecting and integrating light emission over an extended period of time as an indication of the presence of microbes in the sample.

The chemical and enzymatic triggering of 1,2-dioxetanes is set forth in great detail by Schaap et al in Tetrahedron Letters, Vol. 28, No. 9, pp. 935-938, 1987. With regard to the present invention, the CLC, such as the 1,2-dioxetane, is chosen for its chemistry such that the initiation of the chemiluminescent decomposition of the compound is triggered by an enzyme found in the microbe which is to be detected, enumerated, or identified in the sample. Thus, the present invention utilizes a specific relationship between the CLC and enzymes specific to the microbe to be detected, identified, or enumerated. For example, the determination of total bacterial counts could utilize alkaline phosphatase enzyme. Detection of coliforms in water, waste water, and food, etc., could utilize beta galactosidase. Detection of *E. coli* in water, waste, food, etc. could utilize beta glucuronidase. The detection of *L. monocytogenes* in water and food can be detected by the enzymes esculinases, lipases, or proteases. Detection of Salmonella sp in food and water can utilize beta galactosidase, and C8 esterase. Detection of Klebsiella/Proteus in water, clinical samples, etc. can utilize beta xylosidase. The detection of yeast in food, beverages, etc. can use invertase as the useful enzyme. Detection of *Staphylococcus aureus* in clinical samples would utilize the enzyme coagulase. Of course, there are many other forms of microbes which can be detected by various enzymes which identify and characterize the microbes. Further, it is necessary for these enzymes not only to characterize a microbe from other microbes but also from the sample ingredients being tested. In other words, the characterizing enzyme of the microbe which triggers the initial chemiluminescent decomposition of CLC must also characterize the microbe over the food sample, water sample, etc. That is, it is undesirable for any enzymes or another component in the sample to significantly trigger the chemiluminescent decomposition of the CLC.

The light emission from the triggered chemiluminescent decomposition of the CLC is detected and integrated over an extended period of time as an indication of the presence of microbes in the sample. Unlike prior assays using luminol, luminol having a very rapid light emission time span, the present invention utilizes CLC having an extended light emission time period such that detection and integration of the light emission can take place over a period of time from minutes to several hours.

More specifically, luminol chemiluminescence has been used for a number of years in methods based on detecting the amount of hydrogen peroxide consumed by growing bacteria. The hydrogen peroxide is detected by a luminol/peroxidase mixture with the resulting chemiluminescence being proportional to the amount of peroxide present in the system. Although this approach has been useful in labeling immunoglobulins in immunoassays, its usefulness for the direct detection of bacteria has several disadvantages. Besides the rapid light emission which requires the entire reaction to take place before a photosensor, luminol can oxidize in the presence of cations under alkaline conditions. Further, there is non-enzymatic oxidation of the luminol by hemeproteins, short reagent shelf life, and the requirement for a two step procedure as light production with luminol occurs only at a high pH which is incompatible with activity of the oxidase enzymes and with the direct measurement of bacteria in growth media. Further, there is oxidation of luminol by the non-microbial peroxidases/catalases.

Many of these problems have been overcome by the use of 1,2-dioxetane chemiluminescent enzyme substrates. Unlike luminol, these substrates have a long shelf life and are not readily oxidized by hemeproteins or other food components. Further, these substrates offer greater sensitivity and specificity as they can be synthesized for a variety of hydrolytic enzymes as discussed above. Two such dioxetane enzyme substrates (adamantyl 1-1,2-dioxetane phosphate), (PPD (AMPPD) and phenyl galactose substituted dioxetane (adamantyl 1-1,2-dioxetane galactose (GPD (AMPGD) have been found to detect $10^{-21}$ mole of alkaline phosphatase and $10^{-19}$ mole of beta galactosidase, respectively. Accordingly, these photometric enzyme assays offer $10^2$ to $10^6$ greater sensitivity than can be accomplished with colorimetric, radiometric, and fluorometric enzyme assays. Further, since it is undesirable to use radioisotope utilizing assays in such environments as restaurants and the like, the present invention provides an extremely sensitive yet commercially desirable method of detecting bacteria in samples, such as food stuffs and the like.

In conducting the inventive method, a sample, such as a food sample from a source of food in a restaurant, would be taken. The sample would be placed in growth media allowing the optimal production of the specific enzyme by the bacteria in the sample. That is, the sample would be placed under conditions which would promote enzyme production by a bacteria in the sample and prevent suppression of the enzyme production. Ideally this growth medium will promote rapid enzyme production by the test organisms while preventing the growth of other organisms.

For example, for the detection of total bacterial count, using chemiluminescent 1,2-dioxetane enzyme substrate the alkaline phosphates activity is measured. Bacteria are grown in a minimal, well-defined medium that contains cations (e.g., $Zn^{2+}$, $Mg^{2+}$) which are normally required by alkaline phosphatases as cofactors, a carbon source (preferably glucose) and a nitrogen source (either peptone or another organic/inorganic nitrogen supplement). This medium lacks inorganic phosphate as it is inhibitory to phosphatases and it contains inosine which acts as a scavenger of free inorganic phosphates which may be present as contaminants of the medium constituents. The pH of this medium is buffered to an alkaline pH which is compatible with bacterial growth and with the optimal alkaline phosphatase production and activity.

Another example is the medium used for the detection of coliforms, the medium being designed for the optimal production of beta galactosidase. A minimal medium, buffered at neutral pH which contains ortho-nitrophenyl-beta-D-galactoside (ONPG) as the carbon source as well as a gratuitous inducer isopropyl-beta-D-thiogalactopyranoside (IPTG) or another thiogalactoside is utilized. The medium is supplemented with a variety of cations as well as a nitrogen source (tryptone, peptone, casamino acids, $NH_4Cl$, etc). Bile salts and sodium deoxycholate are added to the medium to prevent the growth of gram positive organisms.

A similar approach to the one outlined above can be utilized for media optimization for the production of beta glucuronidase by simply changing the primary carbon source in the medium and proper selection of inducer (e.g., methyl beta glucuronide). The key to the successful design of media for the proper induction of beta galactosidase and beta glucuronidase lies in omitting glucose as well as other readily metabolized carbon sources as they tend to exert catabolite repression on these two enzymes as well as a number of other glycohydrolases. In *E. coli*, catabolite repression of beta galactosidase and beta glucuronidase can be alleviated by growing cells on primary carbon sources (i.e. glycerol, succinate) which result in high intracellular levels of adenosine - 3', 5'- phosphate (c AMP). The media should also be supplemented with a gratuitous inducer for the above two enzymes. The combined effect of the inducer and high levels of c AMP have been demonstrated to optimize the expression of the lac z gene and the uid A gene products.

The step of enriching the amount of enzyme in the sample can be conducted prior to the step of combining the CLC with the sample or after the CLC has been combined. In either event, the sample is incubated under conditions of temperature for one to six hours. Normally, the cells would be incubated at a temperature of approximately 35° C., although temperatures for various samples may vary depending upon the nature of the bacteria to be detected and the nature of the sample itself.

The sample would be incubated during the enriching step in the growth media at a biological pH suitable for inducing the synthesis of the enzyme. Preferably the pH would be approximately neutral. During this period, there would be initial triggering of the chemiluminescent decomposition of the CLC if present. Alternatively, if the CLC is added in after the enrichment step, there would again be initiation of the chemiluminescent decomposition of the CLC upon the exposure of the CLC to the enzymes. Another key to the success of this assay is the availability of the enzymes, produced by the microorganisms, to decompose the 1,2-dioxetanes thereby producing the chemiluminescence. In many cases such enzymes need to be released from the microbial cells by lysis of the cells.

Detection and integration is accomplished by changing the pH of the media to optimize the light emission from the CLC that was initially decomposed by the specific microbial enzyme in the sample. This would be accomplished by after initially incubating the sample at a substantially neutral pH, then changing the pH to an alkaline pH to optimize light emission. The enhancer system would be added, as described in the above referenced article to Schaap et al in Clinical Chemistry, Vol. 5, 1989.

Because of the above procedure utilizing the pH change and enhancer system which can be added after the enrichment step, and because the light emission resulting from the change of pH and enhancer system lasts for minutes to hours, the detection and integration steps can be performed over this extended period of time. Because of the length of this period for integration of light emission, the present invention provides significant sensitivity with regard to the presence of bacteria in the sample. As stated above, this sensitivity is a significant improvement over prior art systems, the sensitivity being approximately equivalent to that obtained by radiometric methods.

It is necessary to expose the CLC to the microbial enzymes. This can be accomplished either by incubating the samples with the CLC such that the microbes take up the CLC or by releasing the enzymes from the microbes into the media. In order to release the enzymes into the media for exposure to the CLC, various methods can be used. For example in the case of gram negative bacteria, the outer membrane of the bacteria can be removed by methods known to the art thereby releasing the enzymes from the periplasmic space of these bacteria. For example, the outer membrane can be removed by the use of various enzymes capable of outer membrane digestion and specific therefore. It is necessary that these enzymes not react with the CLC. An example of such an enzyme is the widely used bacterial cell wall lytic enzyme, lysozyme. The removal of the outer membrane can be accomplished specifically by an EDTA wash step, gentle sonication for one to several minutes, mild lysozyme treatment (concentration of enzyme used varies with cell counts and organism), detergents such as Triton X-100, SDS, sodium deoxyoholate, and CETAB, and/or Organic solvents such as toluene, xylene, chloroform or DMSO. In gram positive bacteria, one or more of the following methods can be used specifically: detergents (as discussed above), osmotic shock, a number of salts such as sodium chloride or potassium chloride, sonication of one to five minutes, organic solvents as discussed above, or extensive lysozyme treatments. The lysis step can be done as a separate step prior to the enzyme assay or as a part of the assay procedure.

Various bacteria are particularly sensitive to various types of digestion or osmotic shock. For example, gram negative bacteria are particularly well adapted to release enzymes by the removal of their outer membrane thereby releasing the enzymes from the periplasmic space of the bacteria. Gram positive bacteria can release enzymes by either being exposed to the detergent, by osmotically shocking the bacteria, by sonically lysing the bacteria, by exposing the bacteria to organic solvent, or by exposing the bacteria to lysozyme.

Alternatively, the cell membrane can be made to "leak" enzymes therefrom by causing ruptures the cell membranes which would result in release of bacterial cytosolic enzyme from the cytoplasm of the bacteria. This can also be accomplished by osmotic shock methods. These methods are very well known in the art, Neu et al, "The Release of Enzymes from *Escherichia coli* by Osmotic Shock and During the Formation of Spheroplasts", *Journal of Biological Chemistry*, Vol. 240, pp. 3685-3692 (1965); Putnam et al, "Complications in the Simplest Cellular Enzyme Assay: Lysis of *Escherichia coli* for the Assay of beta-Galactosidase", *Analytical Biochemistry* Vol. 63, pp. 350-360 (1975); Chassy et al, "Methods for the Lysis of Gram-Positive, Asporogenous Bacteria with Lysozyme", *Applied and Environmental Microbiology*, Vol. 39, pp. 153-158 (1980).

As stated above, the optimal assay conditions once the enzyme has initiated chemiluminescent decomposition of the CLC when the CLC is a 1,2-dioxetane is the use of the appropriate alkaline pH buffer with at least a minimal ionic strength (50 mM), cation ($Zn^{2+}$, $Mg^{2+}$, other cations required by enzyme) substrate concentration and enhancer formulations as discussed above. For example, the use of phosphate buffers or chelating agents is to be avoided as these buffers and agents are inhibitory to alkaline phosphatase activity while the use of enhancers in the assay buffer system is necessary to insure optimal detection during photometric measurement of the alkaline phosphatase reaction as discussed above.

To achieve optimal measurement during detection and integration of the emitted light, a camera, luminometer, or other light intensity measurement device that can integrate over a period of minutes to hours can be used. An important advantage of the use of the combination of a camera with 1,2-dioxetane substrate and enhancers is that a reaction can be monitored for up to a period of two hours without a substantial loss of light intensity. In other words, the shutter of the camera is open for an extended period of time, extending from minutes to several hours and the film being exposed to the light detects and effectively integrates the light emission over the extended period of time. Thusly, the film acts to detect and integrate the emitted light resulting in a measurement in the form of an indication of exposure or nonexposure if there is bacteria present or not present, respectively. The greater the indication of exposure, such as a white spot on a dark film, the greater the indication of the amount of bacteria present. The creation of the exposed area is used to show the detection of the bacteria whereas no light exposure registered on the film would of course show the absence of bacteria. Accordingly, the process is used as a detection method. When a luminometer is used to integrate the light, the amount of light emitted (in mv), under a standard set of conditions, is proportional to the number of organisms in the sample. Therefore, it is possible to generate a standard curve relating the number of organisms to light emitted. If various enzymes are used in combination with various selective media, as discussed above, which are characteristic of various bacteria, the indication of light emitted in the presence of a particular enzyme would be an indication of the identity of the bacterium. Thus, the present invention can be used to enumerate, detect, or identify bacteria.

The present invention outlined above provides a chemiluminescent based assay using triggerable 1,2-dioxetane enzyme substrates for beta galactosidase and beta glucuronidase to detect coliforms and *E. coli*, respectively. The approach incorporates a number of key steps to optimize induction, release and measurement of beta galactosidase and beta glucuronidase activities in *E. coli* and other coliforms.

In this method, optimal conditions for the maximal induction of beta galactosidase and beta glucuronidase are accomplished by the use of two separate optimized, preferably selective, media containing a gratuitous inducer and/or substrates which are readily cleaved by these two enzymes. For beta galactosidase, (isopropyl-beta-D-thiogalactopyranoside/ortho-nitrophenyl-beta-D-galactoside) IPTG/ONPG is used. For beta glucuronidase, methyl beta glucuronide and para nitrophenyl beta glucuronide or MUG is used. To achieve optimal release of the beta glucuronidase from *E. coli* and other coliforms, a lysing mixture is used that contains one or more of an organic solvent, salt, detergent, or reducing agent. Preferably, the applicant's method as used in tests is a formulation that contains 2-beta mercaptoethanol, 20 mM Mn $SO_4$/toluene/10% SDS in a ratio of 5:1:1:1 (v/v/v/v).

Other methods that can be used to lyse cells can involve enzymatic digestion with lysosyme or EDTA wash in combination with gentle sonication and osmotic shock.

The above two approaches can be done preferably as a separate step, although its possible to incorporate some of their elements directly into the assay buffer system.

For optimal assay conditions, appropriate acidic to neutral pH buffer systems of a minimal ionic strength (50 mM), cation such as magnesium cations, reducing agents such as 2-beta mercaptoethanol or dithiothreitol (DTT), temperature of incubation at room temperature or 30° C., substrate concentration of 1-10 mM, and stop reaction solutions of 1M $Na_2CO_3$ or an alkaline-enhancer solution are used.

Optimal measurements are made by cameras, luminometers or other light intensity measuring devices that can integrate over minutes to hours as discussed above. The chemiluminescent 1,2-dioxetane enzyme substrate when used with the proper enhancer formulations as discussed above can be monitored with the camera or luminometer system for up to two hours with little decrease in signal intensity.

EXPERIMENTAL EXAMPLES

The organism selected in this example was *Escherichia coli* strain LE 392. This organism was grown in medium A as described by Csopak et al. (Acta Chemica Scandinavica 26:2401-2411, 1972). This medium contains the following: 0.12M Tris, 0.08M NaCl, 0.02M KCl, 0.02M $NH_4Cl$, 0.003M $Na_2SO_4$, 0.001 M $MgCl_2$, $2.0\times10^{-4}$M $CaCl_2$, $2.0\times10^{-6}$M $ZnCl_2$, 0.5% glucose, and 0.5% Difco Bacto peptone. The medium was adjusted to a final pH of 7.4 with HCl. A glucose solution was prepared separately as a sterile 20% solution and added to the medium at the time of incubation. 10 ml of the above medium was inoculated with one loopful of *E. coli* culture maintained at 4° C. in TSB. This culture was allowed to grow overnight and then used to inoculate 100 ml of fresh medium A broth contained in a 250 ml flask. The flask was incubated at 37° C. with vigorous shaking (200 rpm) until an absorbance reading at 650 nm of 0.45-0.60 was obtained (2-3 hours). The above corresponds to approximately $5-6\times10^8$ cfu/ml of *E. coli* cells. A 10 ml aliquot of the above culture was then removed and centrifuged at 2,500 rpm for 20 minutes at room temperature. The pellet was washed 2× as above with 50 mM Tris buffer pH 8.0 at room temperature. The 2× washed pellet was resuspended in 1 ml of the same buffer and serially diluted ($10^1$, $10^2$, etc.). The above dilutions were assayed directly for alkaline phosphatase activity by adding 10 μl of culture filtrate, 90 μl of Tris buffer, and 150 μl of chemiluminescent 1,2-dioxetane aryl phosphate (Lumiphos 530, Lumigen, Inc., Detroit, Mich.). Incubations were performed in a specialized tray made to fit a Polaroid camera supplied by Analytical Luminescence Laboratory (A. L. L., San Diego, Calif.). The camera was tilted to allow the mixing of reagents and light emission was measured with a high-speed film (Polaroid F12, ASA 20,000) for 5 to 30 minutes. The detection sensitivity using the camera was $10^4$ to $10^5$ cfu/ml for washed cells as compared with $10^2$ to $10^4$ for unwashed cells grown in the same medium (utilizing equal time intervals for light exposure).

Photometric measurements of alkaline phosphatase activity in whole cells were also carried out using a luminometer (A. L. L., San Diego, Calif.). Measurements were conducted following addition of 10 ul aliquots of undiluted or serially diluted cells to 490 ul of substrate (Lumiphos 530, Lumigen, Inc. Detroit, Mich.). The detection sensitivity using a luminometer also approached $10^3$-$10^4$ cfu/ml in 30 minutes at room temperature. Greater sensitivity with chemiluminescent 1,2-dioxetanes can be expected at 37° C. as that the increase in incubation temperature will lead to at least a doubling in enzyme reaction rates.

To demonstrate the importance of growth medium in the assay several experiments were conducted wherein the optimal medium was compared to a good growth medium (Tryptic Soy Broth, TSB). For the alkaline phosphatase assay, in every instance where cells were grown in TSB, no alkaline phosphatase activity was detected by the photometric assay, regardless of numbers of organisms present. However, cells grown in the optimized medium were readily detected in photometric measurements using camera/luminometer. Furthermore, aliquots of cells grown overnight in TSB or the optimized alkaline phosphatase medium and transferred into fresh optimal alkaline phosphatase medium exhibited different time intervals before alkaline phosphatase activity was detected by the photometric assay. Cells grown in TSB and transferred to the optimal medium had much lower enzyme levels initially than cells grown in optimal medium. In one experiment, almost total suppression of alkaline phosphatase activity was observed when larger inoculum (3%) volume of cells grown in TSB was used.

This data is consistent with the need for optimization of medium for the production of alkaline phosphatase in order to prevent end product inhibition by inorganic phosphates and/or other phosphorylated constituents present in widely used enrichment media.

In the chemiluminescent 1,2-dioxetane based measurements of coliform bacteria for beta galactosidase activity *E. coli* LE 392 was selected. This organism was grown in a selective coliform medium (Difco), the composition of which was described in Firstenberg-Eden et al. (J. Food Science, 48:1307-1311, 1983). This medium contains the following ingredients per liter: 10 g of proteose peptone #3 (Difco), 6 g of yeast extract , 20 g of lactose, 0.1 g of sodium deoxycholate, 1.0 g of sodium lauryl sulfate, 0.035 g of bromcresol purple and the medium pH is adjusted to 7.0 with NaOH and autoclaved for 15 minutes at 121° C.

25 ml of the above medium were placed into a flask and were inoculated with an overnight culture of *E. coli* LE 392, previously maintained in TSB at 4° C. The freshly inoculated culture was incubated at 37° C. with vigorous aeration (200rpm) until an optical measurement at A650 nm of 0.300-0.500 was reached. The above cell density corresponds to $3-6\times10^8$ cfu/ml of *E. coli* cells. The cells were sedimented by centrifugation at 2500 RPM at room temperature followed by washing of the pellet with two 10 ml aliquots of 20 mM $Na_2HPO_4$ buffer (pH 7.5) at 5° C. at 2500 RPM. Serial dilutions of the washed pellet were made in 20 mM $Na_2HPO_4$ buffer (pH 7.5) and 5 μl aliquots of these dilutions were assayed for beta galactosidase after diluting to a final volume of 25 ul by adding 100 ul of Lumigal (Lumigen, Inc., Detroit, Mich.). Lumigal is phenyl galactose substituted dioxetane as provided by Lumigen, Inc. under the trademark of Lumigen ™ GPD. The above mixtures were made in a tray made to fit a Polaroid camera (A. L. L., San Diego, Calif.) and measurements were conducted for at least 20 minutes at room temperature. The detection sensitivity of beta galactosidase was determined at $10^5$ cfu/ml The detection sensitivity of the assay was improved when the 20 g of lactose in the medium was substituted with 0.5 g. of ONPG and 0.1 g of IPTG was added to the growth medium to induce enzyme production. In addition, a lysis step, such as incubation in the organic solvents chloroform or toluene was incorporated. Further improvements in the detection sensitivity of this enzyme can be obtained by using a two-step procedure where whole cells are incubated with the substrate in 20 mM $Na_2HPO_4$ buffer at 37° C. for 20 minutes followed by the addition of an enhancer solution (a Lumigal butter formulation) and further incubation for 10 to 30 minutes. The combination of using an optimal pH buffer for the enzyme and the addition of the enhancer will permit greater detection sensitivity for whole cell measurements of beta galactosidase activity.

The above working examples demonstrate the present invention to be useful for the detection, as well as enumeration and identification of bacteria in accordance with the present invention.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. A method of detecting hydrolase activity of biologically active microorganisms in a sample, said method including the steps of: combining the sample with 1,2-dioxetane compound (1,2-dc), which decomposes to a light-emitting species by at least one hydrolytic enzyme of the microorganisms in the sample; triggering light emission from the 1,2-dc by said at least one hydrolytic enzyme initiating decomposition of the 1,2-dc; and detecting and integrating the light emission over an extended period of time as an indication of the presence of the hydrolase activity of the microorganisms in the sample by exposing a light-sensitive detector to the emitted light over a period of time, the detector summing the absolute value of the emitted light over time to indicate the presence of the microorganisms.

2. A method as set forth in claim 1 further including the step of enriching the amount of the at least one enzyme in the sample.

3. A method as set forth in claim 2 wherein the enriching step is further defined as enhancing enzyme synthesis by the microorganisms prior to said combining step.

4. A method as set forth in claim 2 wherein said enriching step is further defined as enhancing enzyme synthesis by the microorganisms after said combining step.

5. A method as set forth in claims 3 or 4 wherein said enhancing step is further defined as incubating the sample for one to six hours in a minimal medium containing cations normally required by alkaline phosphatase as cofactors, a carbon source, a nitrogen source, and a scavenger of free inorganic phosphates, the medium lacking inorganic phosphate and being buffered to an alkaline pH, which optimizes enzyme synthesis and prevents repressing by the end product.

6. A method as set forth in claim 2 wherein said detecting and integrating steps further include the step of changing the pH of the media to optimize light emission from the 1-2-dioxetane compound that was initially decomposed by said at least one hydrolytic enzyme in the sample to produce chemiluminescence.

7. A method as set forth in claim 6 wherein said incubating and changing steps are further defined as incubating the sample in media initially at a neutral pH and changing the pH of the media to an alkaline pH to optimize light emission.

8. A method as set forth in claim 1 further including the step of releasing intracellular enzyme of the microorganisms prior to said combining step.

9. A method as set forth in claim 8 wherein the microorganisms are gram negative bacteria, said releasing step being further defined as removing an outer membrane from the bacteria and releasing the at least one enzyme from the periplasmic space of the bacteria.

10. A method as set forth in claim 8 wherein the microorganisms are gram positive bacteria, said releasing step being further defined as exposing the bacteria to a detergent.

11. A method as set forth in claim 8 wherein the microorganisms are gram positive bacteria, said releasing step being further defined as osmotically shocking the bacteria.

12. A method as set forth in claim 8 wherein the microorganisms are gram positive bacteria, said releasing step being further defined as sonically lysing the bacteria.

13. A method as set forth in claim 8 wherein the microorganisms are gram positive bacteria, said releasing step being further defined as exposing the bacteria to lysozyme or other bacterial cell wall lytic enzymes.

14. A method as set forth in claim 1 wherein said detecting and integrating steps are further defined as detecting and integrating light emission over a period of time greater than two minutes.

15. A method as set forth in claim 14 wherein said detecting step is further defined as detecting and integrating light emission over a period between one minute and two hours.

16. A method of identifying hydrolase activity from biologically active microorganisms in biological and non-biological samples, said method including the steps of: combining the sample with a 1-2-dioxetane compound (1,2-dc); hydrolytic enzymes of the microorganisms in the sample initiating decomposition of the 1,2-dc which decomposes to a light-emitting species; and detecting and integrating the light emission over an extended period of time as an indication of the identity of the microorganisms in the sample by exposing a light-sensitive detector to the emitted light over a period of time, the detector summing the absolute value of the emitted light over time to indicate the presence of the microorganisms.

* * * * *